United States Patent
Stergiou et al.

(10) Patent No.: US 9,138,143 B2
(45) Date of Patent: Sep. 22, 2015

(54) ANNOTATING MEDICAL DATA REPRESENTED BY CHARACTERISTIC FUNCTIONS

(75) Inventors: Stergios Stergiou, East Palo Alto, CA (US); Jawahar Jain, Los Altos, CA (US)

(73) Assignee: Fujitsu Limited, Kawasaki-shi (JP)

( * ) Notice: Subject to any disclaimer, the term of this patent is extended or adjusted under 35 U.S.C. 154(b) by 26 days.

(21) Appl. No.: 12/857,719

(22) Filed: Aug. 17, 2010

(65) Prior Publication Data

US 2012/0047136 A1    Feb. 23, 2012

(51) Int. Cl.
*A61B 5/00*    (2006.01)
*G06F 19/00*    (2011.01)

(52) U.S. Cl.
CPC .............. *A61B 5/00* (2013.01); *G06F 19/366* (2013.01); *A61B 2560/0295* (2013.01)

(58) Field of Classification Search
CPC . A61B 5/00; A61B 2560/0295; G06F 19/366
See application file for complete search history.

(56) References Cited

U.S. PATENT DOCUMENTS

| | | |
|---|---|---|
| 3,561,441 A | 2/1971 | Lombardi |
| 3,653,978 A | 4/1972 | Robinson |
| 4,293,783 A | 10/1981 | Patil |
| 4,320,333 A | 3/1982 | Hase |
| 4,354,105 A | 10/1982 | Spirig |
| 4,621,882 A | 11/1986 | Krumme |
| 4,763,018 A | 8/1988 | Moon |
| 5,181,864 A | 1/1993 | Wakino |
| 5,244,141 A | 9/1993 | Doolittle |
| 5,372,224 A | 12/1994 | Samonil |
| 5,392,402 A | 2/1995 | Robrock |
| 5,491,817 A | 2/1996 | Gopal |
| 5,530,807 A | 6/1996 | Baker |
| 5,576,958 A | 11/1996 | Kawakatsu |
| 5,585,636 A | 12/1996 | Dollansky |
| 5,596,766 A | 1/1997 | Jennings |
| 5,675,707 A | 10/1997 | Gorin |
| 5,754,677 A | 5/1998 | Kawada |
| 5,771,225 A | 6/1998 | Iino |
| 5,790,713 A | 8/1998 | Kamada |

(Continued)

FOREIGN PATENT DOCUMENTS

| | | |
|---|---|---|
| EP | 0550809 | 7/1993 |
| GB | 2466341 A | 6/2010 |

(Continued)

OTHER PUBLICATIONS

"Fast and Effective Retrieval of Medical Tumor Shapes," by Korn et al. In: Knowledge and Data Engineering, vol. 10, Is. 6 (1998). Available at: IEEE.*

(Continued)

*Primary Examiner* — Daniel Kinsaul
(74) *Attorney, Agent, or Firm* — Baker Botts L.L.P.

(57) ABSTRACT

According to certain embodiments, a set of samples of sensor data is accessed. The set of samples records medical measurements taken by one or more medical sensors. A characteristic function is generated from the set of samples. The characteristic function indicates whether a given sample is a member of the set of samples. One or more samples of the set of samples that are associated with a given medical annotation are identified according to the characteristic function.

22 Claims, 3 Drawing Sheets

(56) References Cited

U.S. PATENT DOCUMENTS

| | | | |
|---|---|---|---|
| 5,802,523 A | 9/1998 | Jasuja | |
| 5,815,664 A | 9/1998 | Asano | |
| 5,875,311 A | 2/1999 | Bertram | |
| 5,878,218 A | 3/1999 | Maddalozzo | |
| 5,913,214 A | 6/1999 | Madnick | |
| 5,936,750 A | 8/1999 | Yoo | |
| 5,958,052 A | 9/1999 | Bellovin | |
| 5,971,537 A | 10/1999 | Fukuma | |
| 5,974,242 A | 10/1999 | Damarla | |
| 5,976,083 A | 11/1999 | Richardson | |
| 6,110,114 A | 8/2000 | Nock | |
| 6,169,381 B1 | 1/2001 | Arai | |
| 6,172,576 B1 | 1/2001 | Endo | |
| 6,188,786 B1 | 2/2001 | Ueda | |
| 6,282,537 B1 | 8/2001 | Madnick | |
| 6,298,451 B1 | 10/2001 | Lin | |
| 6,306,087 B1* | 10/2001 | Barnhill et al. | 600/300 |
| 6,381,597 B1 | 4/2002 | Lin | |
| 6,389,374 B1 | 5/2002 | Jain | |
| 6,430,558 B1 | 8/2002 | Delano | |
| 6,480,837 B1 | 11/2002 | Dutta | |
| 6,480,860 B1 | 11/2002 | Monday | |
| 6,493,460 B1* | 12/2002 | MacAulay et al. | 382/133 |
| 6,546,385 B1 | 4/2003 | Mao | |
| 6,583,404 B1 | 6/2003 | Sakurai | |
| 6,643,648 B1 | 11/2003 | Ross | |
| 6,701,296 B1 | 3/2004 | Kramer | |
| 6,704,723 B1 | 3/2004 | Alavi | |
| 6,728,727 B2 | 4/2004 | Komine | |
| 6,760,714 B1* | 7/2004 | Caid et al. | 706/14 |
| 6,778,991 B2 | 8/2004 | Tenorio | |
| 6,779,077 B1 | 8/2004 | Bakke | |
| 6,807,265 B2 | 10/2004 | Boehmke | |
| 6,813,731 B2 | 11/2004 | Zahavi | |
| 6,907,386 B1 | 6/2005 | Liggesmeyer | |
| 7,159,059 B2 | 1/2007 | McNeil | |
| 7,219,319 B2 | 5/2007 | Gould | |
| 7,290,229 B2 | 10/2007 | Baumgartner | |
| 7,844,924 B2 | 11/2010 | Sasao | |
| 7,890,896 B2 | 2/2011 | Moon | |
| 7,904,846 B2 | 3/2011 | Thakur | |
| 7,979,819 B2 | 7/2011 | Hopkins | |
| 8,024,693 B2 | 9/2011 | Adams | |
| 8,074,194 B2 | 12/2011 | Moon | |
| 8,099,690 B2 | 1/2012 | Goswami | |
| 8,171,029 B2 | 5/2012 | Marvit | |
| 2001/0005804 A1 | 6/2001 | Rayner | |
| 2002/0091686 A1* | 7/2002 | Keith, Jr. | 707/5 |
| 2002/0106119 A1* | 8/2002 | Foran et al. | 382/133 |
| 2002/0150285 A1* | 10/2002 | Nelson | 382/131 |
| 2002/0169587 A1* | 11/2002 | Emek et al. | 703/2 |
| 2003/0013951 A1* | 1/2003 | Stefanescu et al. | 600/407 |
| 2003/0154476 A1 | 8/2003 | Abbott | |
| 2003/0220926 A1 | 11/2003 | Huelsman | |
| 2003/0229278 A1* | 12/2003 | Sinha | 600/407 |
| 2004/0093093 A1 | 5/2004 | Andrews | |
| 2004/0139136 A1 | 7/2004 | Goubin | |
| 2004/0147840 A1* | 7/2004 | Duggirala et al. | 600/437 |
| 2004/0181500 A1 | 9/2004 | Huelsman | |
| 2004/0193036 A1* | 9/2004 | Zhou et al. | 600/407 |
| 2004/0199332 A1* | 10/2004 | Iliff | 702/19 |
| 2004/0220975 A1 | 11/2004 | Carpenter | |
| 2004/0260667 A1 | 12/2004 | Huelsman | |
| 2005/0126306 A1 | 6/2005 | Wang | |
| 2006/0112119 A1 | 5/2006 | Vian | |
| 2006/0120137 A1 | 6/2006 | Gould | |
| 2006/0274928 A1* | 12/2006 | Collins et al. | 382/132 |
| 2007/0021689 A1 | 1/2007 | Stergiou | |
| 2007/0118339 A1 | 5/2007 | Moon | |
| 2007/0150429 A1 | 6/2007 | Huelsman | |
| 2007/0167844 A1 | 7/2007 | Asada | |
| 2007/0204020 A1 | 8/2007 | Anderson | |
| 2007/0214439 A1 | 9/2007 | Reis | |
| 2007/0276970 A1 | 11/2007 | Werner | |
| 2008/0112627 A1 | 5/2008 | Oda | |
| 2008/0243746 A1 | 10/2008 | Stergiou | |
| 2008/0249379 A1 | 10/2008 | Furman | |
| 2008/0270337 A1 | 10/2008 | Huelsman | |
| 2008/0282207 A1 | 11/2008 | Baumgartner | |
| 2009/0037859 A1 | 2/2009 | Thakur | |
| 2009/0055458 A1 | 2/2009 | O'Neil | |
| 2009/0069637 A1 | 3/2009 | Healey | |
| 2009/0077104 A1 | 3/2009 | Sheets | |
| 2009/0094262 A1 | 4/2009 | Marvit | |
| 2009/0117288 A1 | 5/2009 | Gluck | |
| 2009/0210470 A1 | 8/2009 | Sarlos | |
| 2009/0226065 A1* | 9/2009 | Chen | 382/131 |
| 2009/0254513 A1* | 10/2009 | Luukkala et al. | 707/2 |
| 2009/0313201 A1 | 12/2009 | Huelsman | |
| 2009/0327733 A1 | 12/2009 | McDougal | |
| 2010/0017175 A1 | 1/2010 | Moon | |
| 2010/0036815 A1* | 2/2010 | Tago et al. | 707/3 |
| 2010/0036835 A1 | 2/2010 | Stergiou | |
| 2010/0050145 A1 | 2/2010 | Baumgartner | |
| 2010/0115476 A1 | 5/2010 | Adams | |
| 2010/0192116 A1 | 7/2010 | Hopkins | |
| 2011/0055545 A1 | 3/2011 | Sovio et al. | |
| 2011/0099175 A1 | 4/2011 | Darcy | |
| 2011/0161285 A1* | 6/2011 | Boldyrev et al. | 707/609 |
| 2011/0264804 A1 | 10/2011 | Vuksan | |

FOREIGN PATENT DOCUMENTS

| | | | |
|---|---|---|---|
| JP | 2003-527922 | 9/2003 | A61B 5/00 |
| JP | 2005-508556 | 3/2005 | A61B 5/00 |
| JP | 2007-528746 | 10/2007 | A61B 5/00 |
| JP | 2010-519616 | 6/2010 | A61B 5/002 |
| WO | 00/26824 | 5/2000 | |
| WO | 2005/088473 | 9/2005 | |
| WO | 2008/099290 | 8/2008 | |

OTHER PUBLICATIONS

"Selective min-terms based tabular method for BDD Manipulations," by Prasad et al. In: World Academy of Science, Engineering and Technology (2005). Availablet at: http://citeseerx.ist.psu.edu/viewdoc/download?doi=10.1.1.193.698&rep=rep1&type=pdf Last visited: Oct. 7, 2012.*

"Boolean Matching using Binary Decision Diagrams with Applications to Logic Synthesis and Verification," by Lai et al. In: Computer Design: VLSI in Computers and Processors (1992). Available at IEEE.*

"A Characterization of Binary Decision Diagrams," by Chakravarty, Sreejit. In: IEEE Transactions on Computers, vol. 42, No. 2 (1993). Available at: IEEE.*

"Binary Decision Diagram—Wikipedia Revision Jun. 16, 2009," by Wikipedia (2009). Available from the version history the entry at: http://en.wikipedia.org/w/index.php?title=Binary_decision_diagram&oldid=296815963.*

"Range Query—Wikipedia Revision May 2, 2008," by Wikipedia (2008). Available from the version history for the entry at: http://en.wikipedia.org/w/index.php?title=Range_query&oldid=209708286.*

BDD (JavaBDD 2.0 API), by Whaley, John. 2008 (evidenced by Internet Archive Capture from Oct. 26, 2008). Originally available at: http://javabdd.sourceforge.net/apidocs/net/sf/javabdd/BDD.html.*

U.S. Appl. No. 12/857,613, by inventors Stergios Stergiou et al., entitled "Annotating Binary Decision Diagrams Representing Sensor Data," 40 pages, filed Aug. 17, 2010.

U.S. Appl. No. 12/857,768, by inventors Stergios Stergiou et al., entitled "Annotating Environmental Data Represented by Characteristic Functions," 41 pages, filed Aug. 17, 2010.

Deshpande, Amol et al., "Model-Based Querying in Sensor Networks," *University of Maryland*, 2010.

Gray, Alasdair J. G. et al, A Semantically Enabled Service Architecture for Mash Ups over Streaming and Stored Data, 8th Extended Semantic Web Conference, Heraklion, Greece, 2011.

Liu, Mengmeng et al., "Maintaining Recursive Views of Regions and Connectivity in Networks," *IEEE Transactions on Knowledge and Data Engineering*, 22 (8), Aug. 2010.

(56) References Cited

OTHER PUBLICATIONS

Tran, Duc A. et al., "Enabling Publish/Subscribe Services in Sensor Networks," University of Massachusetts, Boston and IBM Zurich Research Laboratory, Switzerland, 2010.
Search Report for GB1114161.1, Dec. 15, 2011.
Search Report for GB1114155.3, Dec. 15, 2011.
Search Report for GB1114028.2, Dec. 8, 2011.
Search Report for GB1113969.8, Nov. 15, 2011.
Search Report for GB1113967.2, Nov. 24, 2011.
Teslenko, Maxim et al., "Computing a Perfect Input Assignment for Probabilistic Verification," *VLSI Circuits and Systems II, Proceedings of SPIE*, v. 5837, 2005.
Jain, Jawahar et al., "Probabilistic Design Verification," *IEEE International Conference on ICCAD-91 Digest of Technical Papers*, Section 2.2, Properties of Hash Codes, 1991.
Kowshik, Hemant et al., "Zero-error Function Computation in Sensor Networks," *Joint 48th IEEE Conference on Decision and Control and 28th Chinese Control Conference*, Shanghai, 2009.
Office Action for U.S. Appl. No. 12/857,655, Dec. 23, 2011.
U.S. Appl. No. 13/241,698, filed Sep. 23, 2011, Stergiou.
U.S. Appl. No. 13/241,789, filed Sep. 23, 2011, Stergiou.
U.S. Appl. No. 13/241,872, filed Sep. 23, 2011, Stergiou.
U.S. Appl. No. 13/241,991, filed Sep. 23, 2011, Stergiou.
U.S. Appl. No. 13/242,095, filed Sep. 23, 2011, Stergiou.
U.S. Appl. No. 13/242,253, filed Sep. 23, 2011, Stergiou.
U.S. Appl. No. 13/243,104, filed Sep. 23, 2011, Stergiou.
U.S. Appl. No. 13/243,158, filed Sep. 23, 2011, Stergiou.
U.S. Appl. No. 13/243,271, filed Sep. 23, 2011, Stergiou.
Search Report for GB 1114027.4, Nov. 17, 2011.
Hlavička, Jan et al., "Algorithm for Minimization of Partial Boolean Functions," Czech Technical University, Prague, Apr. 2, 2000.
Search Report for GB1114025.8, Nov. 21, 2011.
Cayirci, Erdal, "Distributed Spatial Data Aggregation and Dilutions Based on Hashing and Relational Algebra in Wireless Sensor Networks," *Proceedings of ISSNIP*, Dec. 2004.
U.S. Appl. No. 12/857,594, filed Aug. 17, 2010, Stergiou.
U.S. Appl. No. 12/857,603, filed Aug. 17, 2010, Stergiou.
U.S. Appl. No. 12/857,628, filed Aug. 17, 2010, Stergiou.
U.S. Appl. No. 12/857,655, filed Aug. 17, 2010, Stergiou.
U.S. Appl. No. 12/857,690, filed Aug. 17, 2010, Stergiou.
"Binary Decision Diagram", http://en.wikipedia.org/w/index.php?oldid=372197325, Feb. 14, 2011.
Chen; Efficient Algorithms for Pattern Matching on Directed Acyclic Graphs; 21st International Conference on Data Engineering, Apr. 2005.
Deshpande, et al; Model-Driven Data Acquisition in Sensor Networks; Proceedings of the 30th VLDB Conference, Toronto, Canada, 2004.
"Hash Function", http://en.wikipedia.org/w/index.php?oldid=375246104.
Turton; Extending Quine-McCluskey for Exclusive-Or Synthesis; IEEE Transactions on Education, vol. 39, Issue 1; pp. 81-85, 1996.
Li et al.; Nonthreshold-Based Event Detection for 3D Environment Monitoring in Sensor Networks; IEEE Transactions on Knowledge and Data Engineering; vol. 20; No. 12; pp. 1699-1711; Dec. 2008.
Xue et a l.; Contour Map Matching for Event Detection in Sensor Networks; SIGMOD 2006; pp. 145-156, 2006.
Gupchup et al.; Model-Based Event Detection in Wireless Sensor Networks; Proceeding of the Workshop for Data Sharing and Interoperability on the World Wide Web, 2009.

Krenz, Rene et al.; "Improved Boolean Function Hashing based on Multiple-Vertex Dominators," *IEEE Design Automation Conference*, vol. 1, 573-578, 2005.
Sun, Z., et al., "Medical Image Compression Based on Ordered Binary Decision Diagrams," *IEEE First International Workshop on Education Technology and Computer Science*, 2009.
Search Report for GB1114026.6.
Office Action for U.S. Appl. No. 12/857,613, Jan. 31, 2012.
Office Action for U.S. Appl. No. 12/857,603, Feb. 17, 2012.
Office Action for U.S. Appl. No. 12/857,594, Mar. 14, 2012.
Office Action for U.S. Appl. No. 12/857,655, Jun. 13, 2012.
Office Action for U.S. Appl. No. 12/857,594, Aug. 13, 2012.
Office Action for U.S. Appl. No. 12/857,603, Jul. 27, 2012.
Office Action for U.S. Appl. No. 12/857,768, Jul. 25, 2012.
Office Action for U.S. Appl. No. 12/857,628, Jan. 23, 2013.
Office Action for U.S. Appl. No. 12/857,628, Apr. 15, 2013.
Office Action for U.S. Appl. No. 12/857,690, Jan. 23, 2013.
Office Action for U.S. Appl. No. 12/857,690, Apr. 15, 2013.
Office Action for U.S. Appl. No. 12/857,768, Dec. 17, 2012.
Office Action for U.S. Appl. No. 13/243,158, Dec. 26, 2012.
Office Action for U.S. Appl. No. 13/243,158, Apr. 12, 2013.
Notice of Allowance for U.S. Appl. No. 12/857,655, Mar. 20, 2013.
Louis Kruger, et al., *"Secure Function Evaluation with Ordered Binary Decision Diagrams," CCS'06*, Oct. 30-Nov. 3, 2006; 11 pgs., 2006.
Rolf Drechsler, et al., *"Binary decision diagrams in theory and practice,"* Int. J STTT (2001) 3:112-136, 25 pgs., May 15, 2001.
Srcejit Chakravarty, *"A Characterization of Binary Decision Diagrams,"* IEEE Transactions on Computers, vol. 42, No. 2, 9 pgs., Feb. 1993.
Bhaskar Saha, *"A Model-Based Reasoning Architecture for System-Level Fault Diagnosis,"* School of Electrical and Computer Engineering, Georgia Institute of Technology, 106 pgs., Apr. 2008.
Non-Final Office Action for U.S. Appl. No. 13/241,872, Apr. 4, 2014.
Yaofend Wen, et al., *"Heart rate monitoring in dynamic movements from a wearable system,"* Medical Devices and Biosensors, 2008. ISSS-MDBS 2008. 5th International Summer School and Symposium on, Jun. 1-3, 2008, pp. 272-275, 2008.
D. Michael Miller, et al., *"Implementing a multiple-valued decision diagram package,"* Multiple-Valued Logic, 1998. Proceedings. 1998 28th IEEE International Symposium on, May 27-29, 1998, pp. 52-57, 1998.
Mohamed Raseen, et al., *"Mathematical model to predict the number of nodes in an ROBDD,"* Circuits and Systems, 2004. MWSCAS '04. The 2004 47th Midwest Symposium on, vol. 3, Jul. 25-28, 2004, pp. 111-431-434, 2004.
Stergios Stergiou, et al., *"Dynamically resizable binary decision diagrams,"* GLSVLSI 2010, Proceedings of the 20th symposium on Great lakes symposium on VLSI, pp. 185-190, 2010.
Mathie et al., "Classification of Basic Daily Movements Using a Triaxial Accelerometer", Medical & Biological Engineering & Computing 2004, vol. 42, pp. 679-687, IFMBE, 2004.
Karantonis et al., "Implementation of a Real-Time Human Movement Classifier Using a Triaxial Accelerometer for Ambulatory Monitoring", IEEE Transactions on Information Technology in Biomedicine, vol. 10, No. 1, pp. 15-167, IEEE, 2006.
Office Action for U.S. Appl. No. 12/857,768, Jun. 3, 2013.
Murthy, *"On Growing Better Decision Trees From Data"*, 1997.
Japanese Office Action issued in Patent Appl. No. 2011-177989; 5 pages with English Translation, Jan. 6, 2015.

\* cited by examiner

ANNOTATING MEDICAL DATA REPRESENTED BY CHARACTERISTIC FUNCTIONS

TECHNICAL FIELD

This invention relates generally to the field of data systems and more specifically to annotating medical data represented by characteristic functions.

BACKGROUND

Sensors may be used in different situations (such as medical, environment, and other situations) to take measurements over time. In certain cases, the measurements may yield a relatively large volume of data, which may be difficult to analyze. Techniques may be used to process (such as store, utilize, and/or analyze) large volumes of data.

SUMMARY OF THE DISCLOSURE

In accordance with the present invention, disadvantages and problems associated with previous techniques for processing data may be reduced or eliminated.

According to certain embodiments, a set of samples of sensor data is accessed. The set of samples records medical measurements taken by one or more medical sensors. A characteristic function is generated from the set of samples. The characteristic function indicates whether a given sample is a member of the set of samples. One or more samples of the set of samples that are associated with a given medical annotation are identified according to the characteristic function.

Certain embodiments of the invention may provide one or more technical advantages. A technical advantage of one embodiment may be that sensor data may be represented by a characteristic function that can be stored as a binary decision diagram. Another technical advantage of one embodiment may be that a search query may be represented by a query function. The search query and the characteristic function may be used to obtain sensor values of the sensor data that satisfy the search query.

Another technical advantage of one embodiment may be that model sensor data for a particular annotation may be represented by a particular annotated model characteristic function. The annotated model characteristic function may be combined with a characteristic function to annotate the characteristic function with the annotation. Another technical advantage of one embodiment may be that Boolean functions may be transformed to arithmetic functions. Hash codes may be calculated from the arithmetic functions. If the hash codes are equal, then the Boolean functions may be designated as equivalent.

Certain embodiments of the invention may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION OF THE DRAWINGS

Embodiments of the present invention and its advantages are best understood by referring to FIGS. 1 through 5 of the drawings, like numerals being used for like and corresponding parts of the various drawings.

Figure 1:
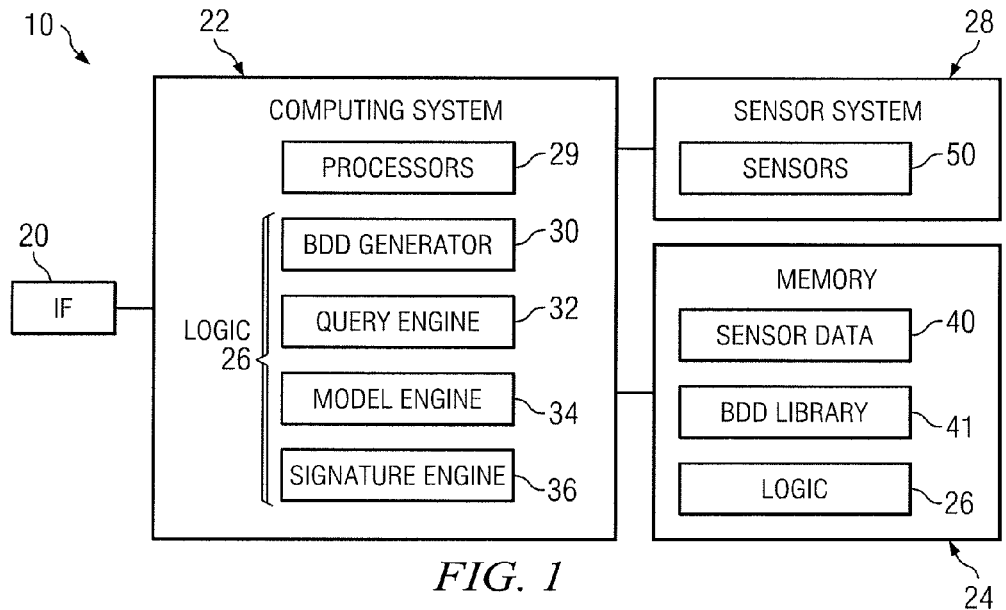
FIG. 1 illustrates an example of system that may be used to process sensor data.

FIG. 1 illustrates an example of system 10 that may be used to process sensor data. In certain embodiments, system 10 may represent sensor data by a characteristic function that can be stored as a binary decision diagram. In certain embodiments, system 10 may represent a search query by a query function. The search query and the characteristic function may be used to obtain sensor values of the sensor data that satisfy the search query.

In certain embodiments, system 10 may represent model sensor data for a particular annotation by a particular annotated model characteristic function. The annotated model characteristic function may be combined with a characteristic function to annotate the characteristic function with the annotation. In certain embodiments, system 10 may transform Boolean functions (such as characteristic functions) to arithmetic functions. Hash codes may be calculated from the arithmetic functions. If the hash codes are equal, then the Boolean functions may be designated as equivalent.

In the illustrated embodiment, system 10 includes an interface (IF) 20, a computing system 22, a memory 24, and a sensor system 28 coupled as shown. Computing system 22 includes one or more processors 29. Logic 26 includes a binary decision diagram (BDD) generator 30, a query engine 32, a model engine 34, and a signature engine 36, and may be stored by computing system 22 and/or memory 24. Memory 24 stores sensor data 40 and a BDD library 41. Sensor system 28 includes one or more sensors 50.

In certain embodiments, sensors 50 of sensor system 28 measure features (such as medical or environmental features) to yield measurements (such as medical or environmental measurements), which are sent to computing system 22. A measurement is typically expressed as a numerical value.

Examples of sensors 50 may include medical, environmental, and/or other suitable sensors. Medical sensors may be used to measure one or more features of a patient's medical state. Medical sensors may include medical monitors, medical laboratory equipment, therapeutic equipment, medical imaging machines, and/or other medical sensor. Examples of medical sensors include electrocardiogram (ECG) sensors, blood pressure sensors, and/or pulse oximetry sensors.

An electrocardiogram sensor records electrical activity of the heart over time through skin electrodes. An electrocardiogram sensor may output tracings of heartbeats. A tracing of a normal heartbeat typically includes a P-wave, a QRX complex (that includes an R-wave), and a T-wave. Samples may record any suitable features of the tracings. For example, samples may record intervals between features of consecutive heartbeats, such as the interval between two consecutive R-waves. The interval may be used to extract information about heart rate and its variability.

A blood pressure sensor may use a sphygmomanometer to measure blood pressure. The measurement may include systolic and/or diastolic values in units of millimeters of mercury (mmHg). In certain instances, blood pressure may be measured at regular intervals throughout the day and night.

A pulse oximetry sensor may be used to measure the oxygenation of hemoglobin. A pulse oximeter may be placed on the skin (such as a fingertip) and transmit a red and an infrared wave. The absorption of the waves may be measured to determine oxygen saturation. The pulse oximeter may output the oxygen saturation as, a percentage from zero percent to ninety-nine percent.

Environmental sensors may measure an environmental feature, for example, such as geographic location, air pressure, elevation, and/or temperature. Examples of environmental sensors include a Global Positioning System (GPS) that determines location, a barometer that measures air pressure, an altimeter that measures elevation, and a thermometer that measures temperature.

Sensor data 40 may include any suitable information. In certain embodiments, sensor data 40 records measurements taken by one or more sensors 50. Sensor data 40 may include samples that may have any suitable format. In certain embodiments, the format of the samples may be a tuple (or ordered set) that has one or more data parameters, and a particular sample may be a tuple of one or more values for the one or more data parameters. For example, a tuple format (t, p) may have data parameters time t and pressure p, and a particular sample (t0, p0) may have values pressure p0 measured at time t0.

The tuple format may include any suitable data parameters, such as one or more sensor parameters and/or one or more test parameters. A sensor parameter may correspond to one or more sensors 50, and a sensor value may record one or more measurements taken by one or more sensors 50. For example, a sensor value may record a measurement taken by a sensor 50. A test parameter may correspond to a factor that describes a temporal, spatial, and/or environmental feature of the measurement process, and a test value may record the value of the feature when the measurements are taken. For example, the parameter may be time, and the parameter value may record a particular time at which measurements are taken.

Examples of temporal features include time, which may be expressed as an absolute time (for example, 2:00 PM, May 25, 2010) or as relative time (for example, time elapsed from a starting time or time remaining until an ending time). Examples of spatial features include location, such as geographical location (which may include longitude, latitude, and/or altitude), location on a body (for example, a human body), and type of location (for example, rural or urban). Examples of environmental features describe physical characteristics of an environment, such as temperature (for example, atmospheric temperature or body temperature).

Model sensor data 40 describes sensor data that may be used to annotate sensor data obtained from measurements in order to categorize the data. For example, certain model sensor data may be categorized and annotated with a "normal" (or similar) annotation, while other sensor data may be categorized and annotated with an "abnormal" (or similar) annotation. Sensor data obtained from measurements that match the normal model sensor data may be categorized as normal, while measured sensor data that match abnormal model sensor data may be categorized as abnormal.

Any suitable annotation may be used. In certain embodiments, medical annotations that may be used to categorize medical sensor data. Examples of medical annotations may include a "normal" annotation for normal sensor data and an "abnormal" annotation for abnormal sensor data. Other examples of medical annotations may include annotations for particular diseases, conditions, symptoms, severity, and/or other category of medical sensor data.

In certain embodiments, environmental annotations that may be used to categorize environmental sensor data. Examples of environmental annotations may include a "normal" annotation for normal sensor data and an "abnormal" annotation for abnormal sensor data. Other examples of environmental annotations may include annotations for particular weather conditions, geographical features, social conditions, and/or other category of environmental sensor data.

Model sensor data includes model samples. A model sample comprises a tuple of one or more model sensor values. A model sensor value represents one or more measurements that could have been taken by one or more sensors. The model samples may be annotated with the annotation to indicate the category to which it belongs.

Binary decision diagram library 41 stores binary decision diagrams. In certain embodiments, a binary decision diagram (BDD) is a rooted directed acyclic graph (DAG) that may be used to represent a Boolean function f. A BDD includes nodes, such as non-terminal (or decision) nodes and terminal nodes, where terminal nodes include root nodes. A non-terminal node corresponds to a sub-function f and is labeled by a Boolean variable $v=x_i$. A non-terminal node has an outgoing 1-edge and an outgoing 0-edge pointing to child nodes. A 1-edge points to the sub-BDD that represents function $v \cdot f$, and a 0-edge 88 points to the sub-BDD that represents function $\bar{v} \cdot f$. In other words, a 1-edge represents an assignment of v to 1, and a 0-edge represents an assignment of v to 0. Terminal nodes include a 0-terminal and a 1-terminal that represent Boolean functions 0 and 1, respectively.

A path from the root node to the 1-terminal represents a set of variable assignments setting the represented Boolean function to 1. A path from the root node to the 0-terminal represents a set of variable assignments setting the represented Boolean function to 0.

In certain embodiments, a BDD is stripped of redundant decision nodes and subgraph isomorphisms. In certain embodiments, an ordered binary decision diagram (OBDD) is a BDD where all paths from the root node to the terminal nodes examine variables in the same order. OBDDs may allow for canonical representations. Other examples of BDDs include reduced ordered BDDs (ROBDDs), partitioned ordered binary decision diagrams (POBDDs), zero-suppressed decision diagrams (ZDDs), nano binary decision diagrams (nanoDDs), zero-suppressed nano binary decision diagrams (nanoZDDs), other suitable binary decision diagrams, and/or a combination of any of the preceding. In a ROBDD, isomorphic subgraphs are not present, and the order of the variables from the root node of the BDD to a terminal node are the same for all paths. In a ZDD, a node is excluded if the node is a negative literal. In other RBDDs, a node is excluded if both edges of the node point to the same node. Examples of the other types of BDDs are described in more detail below.

In certain embodiments, node structure of BDD library 41 includes any suitable information, such as information about each binary variable and indices to the nodes that correspond to the two possible evaluations of the variable. BDD library 41 may also include information about complementation of one of the indices.

In certain embodiments, BDD library 41 may store the information compactly. In certain embodiments, BDD library 41 may maintain the indices and variable identifiers as a function of the size of the BDD. For example, a BDD may have at most k nodes throughout some or all manipulations performed by BDD library 41. Each vertex of the BDD may be labeled with one of at most v variable identifiers.

The indices to nodes therefore require at most $\lceil \log(v) \rceil$ bits to index any variable. The node therefore requires only $2 \cdot \lceil \log(k) \rceil + \lceil \log(v) \rceil$ bits. In addition, two bits may be reserved, one bit used to identify complemented edges and another bit used as a general mark bit used during garbage collection. Values for v and k may be determined in any suitable manner. As an example, a user may specify v and a default k value may be used initially. When the address space allowed by the default k value is exhausted, the k value may be increased and the node table may be rebuilt. As another example, maximum values for v and k may be assumed.

In certain embodiments, BDD generator 30 accesses a set of samples of sensor data that records measurements taken by one or more sensors. BDD generator 30 represents each sample as a minterm to yield a set of minterms. BDD generator 30 generates a characteristic function from the minterms, the characteristic function indicating whether a given minterm is a member of the set of minterms.

In certain embodiments, a characteristic function $f^S$ of a set S indicates whether a given natural (represented by a minterm) is a member of a set S. In certain embodiments, characteristic function $f^S(\bar{x})$ of a set $S \subset \mathbb{N}$ may be the Boolean function such that $f^S(\bar{x})=1$ iff $\bar{x}$ is the binary representation of an element of S. For example, for $S=\{1,3\}$, $f(0,0)=f(1,0)=0$ and $f(0,1)=f(1,1)=1$.

A minterm is a logical expression of n variables that employs only the complement operator and the conjunction operator. For a Boolean function of n variables, a minterm is a product term in which each of the n variables appears once, either in a complemented or uncomplemented form.

In certain embodiments, query engine 32 receives a search query for a search of a set of samples of sensor data. The search query indicates one or more requested values of one or more parameters. The samples are represented by a characteristic function indicating whether a given binary representation represents a sample of the set of samples. Query engine 32 formulates a query function representing the requested values. Query engine 32 uses the query function and the characteristic function to identify one or more samples that have the one or more requested values.

In certain embodiments, model engine 34 accesses one or more sets of model samples of model sensor data. Each set comprises model samples for a corresponding annotation of one or more annotations. Model engine 34 performs the following for each set to yield one or more annotated model characteristic functions: represent each model sample of the each set as a model minterm to yield a set of model minterms; generate a model characteristic function from the model minterms, the characteristic function indicating whether a given minterm is a member of the set of model minterms; and annotate the model characteristic function. Model engine 34 generates a general model characteristic function from the annotated model characteristic functions.

In certain embodiments, signature engine 34 receives a first Boolean function and a second Boolean function, such as first and second characteristic functions. Signature engine 34 transforms the first and second Boolean functions to yield first and second arithmetic functions, respectively. Signature engine 34 provides the same input to the first and second arithmetic functions to calculate first and second hash codes (or "signatures"), respectively. If the first hash code equals the second hash code, signature engine 34 designates the first and second Boolean functions as equivalent. Otherwise, signature engine 34 designates that the first and second Boolean functions are not equivalent.

In certain embodiments, interface 20 receives input from, for example, a user, using any suitable input device and communicates the input to computing system 22. Interface 20 receives output from computing system 22 and communicates the output to computing system 22 using any suitable output device.

Figure 2:
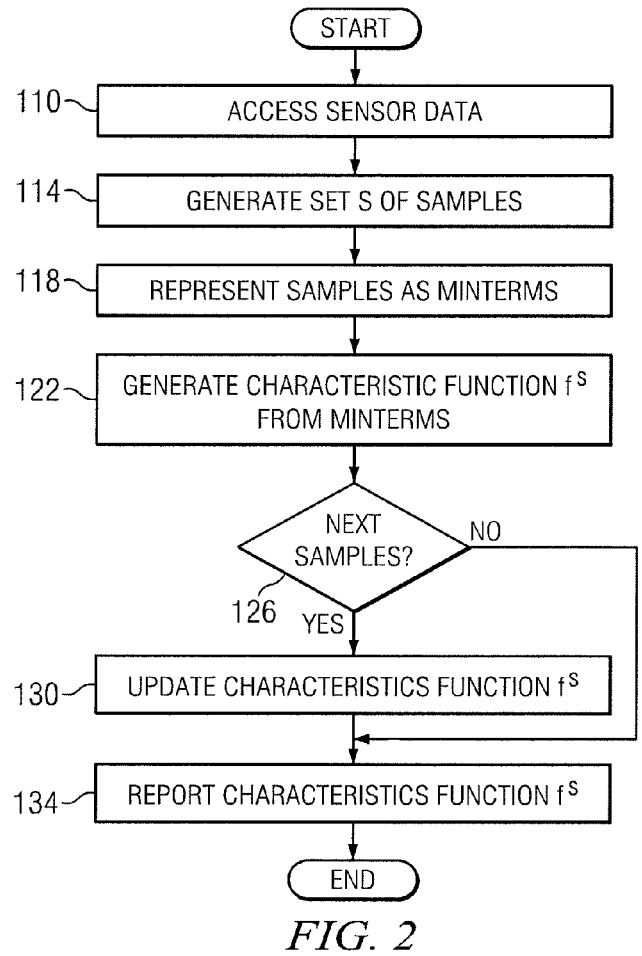
FIG. 2 illustrates an example of a method for representing sensor data by characteristic functions.

FIG. 2 illustrates an example of a method for representing sensor data by characteristic functions. The method may be performed by BDD generator 30. In the method, sensor data 40 is accessed at step 110. Sensor data 40 records measurements taken by sensors 50. For example, sensor data 40 may record measurements taken by a first sensor 50 with a frequency of 1 Hertz and a second sensor 50 with a frequency of 60 Hertz.

A set S of samples is generated from sensor data 40 at step 114. In certain embodiments, each sample comprises a tuple of one or more sensor values. Each sensor value records one or more measurements taken by one or more sensors at a test value of a test parameter. The test parameter may represent time, temperature, or location. The sample tuple may also include the test value.

Set S may be generated in any suitable manner. In certain embodiments, time may be quantized according to the sampling frequencies of sensors 50 and/or desired accuracy. For each time $t_i$, set S of sensor values is obtained to yield $S=\{(t_i, q_i^1, \ldots, q_i^k)\}$, where $q_i^j$ is the quantized input from sensor j at time instance i.

Each sample is represented as a minterm at step 118. The sample may be represented as a minterm in any suitable manner. In certain embodiments, one or more variables are allocated to each data value (for example, a test or sensor value) of a sample. For example, Nt (for example, Nt=32) variables may be allocated for time, Ns1 (for example, Ns1=8) variables for the first sensor, and Ns2 (for example, Ns2=8) variables for the second sensor. In the example, the sample corresponds to a minterm of the form $t_1 \ldots t_{Nt} \cdot s_1^1 \ldots s_{Ns1}^1 \cdot s_1^2 \ldots s_{Ns2}^2$, for example, $t_1 t_2 \ldots t_{32} \cdot s_1^1 \ldots s_8^1 \cdot s_1^2 \ldots s_8^2$.

Each sensor value is expressed as a binary number using the allocated variables. In the example, a subset of S may be $\{(1,70,3), (2,70,3), (3,70,4)\}$. The related minterms are:

00000000000000000000000000000001·01000110·00000011,

00000000000000000000000000000010·01000110·00000011,

00000000000000000000000000000011·01000110·00000100.

Characteristic function $f^S$ is generated from the minterms at step 122. Characteristic function $f^S$ indicates whether a given minterm is a member of the set of minterms. Characteristic function $f^S$ may be generated from the minterms in any suitable manner. In certain embodiments, a logical operation may be applied to the minterms to generate characteristic function $f^S$. A logical operation may be one of or a logical combination of any two or more of the following: AND, OR, XOR, and NOT. In certain embodiments, a logical OR operation may be applied to the minterms to generate characteristic function $f^S$. Applying a logical OR operation to a number of operands yields the logical OR of the operands. The corresponding characteristic function $f^S(\vec{x}; \vec{s}^1, \vec{s}^2)$ is the logical OR of all minterms.

There may be next samples of sensor data 40 at step 126. For example, there may be newer, or more recent, samples in sensor data 40. If there are next samples, the method returns to step 114 to generate a next set S of the next samples. If there are no next samples, the method proceeds to step 130.

Characteristic function $f^S$ is updated using the next samples at step 130. Characteristic function $f^S$ may be updated in any suitable manner. In certain embodiments, steps similar to steps 114 through 122 may be performed. In the embodiments, a set of next samples may be generated. Each next sample may be represented as a next minterm. Characteristic function $f^S$ may be updated using the next minterms. For example, a logical operation (such as a logical OR operation) may be applied to characteristic function $f^S$ and the next minterms to yield an updated characteristic function $f^S$.

Characteristic function $f^S$ is reported at step 134. Characteristic function $f^S$ may be reported in any suitable manner. For example, BDD generator 30 may facilitate display of characteristic function $f^S$ at interface 20.

Figure 3:
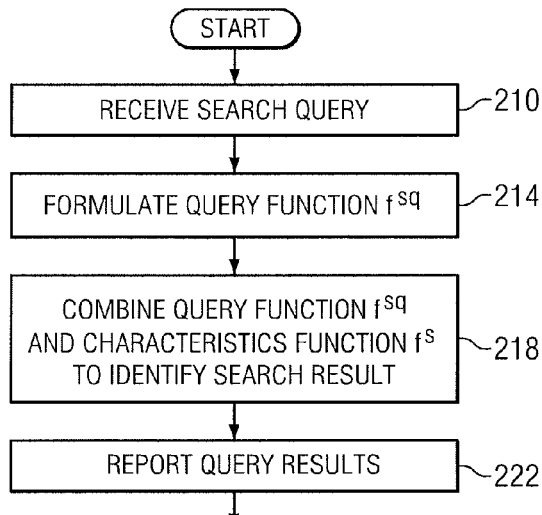
FIG. 3 illustrates an example of a method for querying sensor data represented by characteristic functions.

FIG. 3 illustrates an example of a method for querying sensor data represented by characteristic functions. The method may be performed by BDD generator 30. In the method, a search query is received at step 210. The search query requests a search of a set of samples of sensor data 40 and may have any suitable format. In certain embodiments, the search query may indicate one or more requested values of one or more data parameters, and may request retrieval of samples that satisfy the requested values. A data parameter may be a sensor parameter that corresponds to a sensor and/or a test parameter that describes, for example, a spatial, temporal, and/or geographical feature. The samples of sensor data 40 may be represented by a characteristic function indicating whether a given binary representation represents a sample of the set of samples.

Query function $f_R$ representing the requested values is formulated at step 214. Query function $f_R$ may be used to identify samples (represented by a characteristic function) that have the requested values. Query function $f_R$ may be formulated in any suitable manner. In certain embodiments, each requested value may be expressed as a requested minterm, and a range query function $f_R$ may be formulated from the requested minterms. For example, if the requested values are t=128 through 255, then query function $f_R(\vec{t}; \vec{s}^1; \ldots; \vec{s}^N) = \bar{t}_{31}\bar{t}_{30}\ldots\bar{t}_8\bar{t}_7$.

As an another example, the following method may be used to generate a BDD of a Boolean function $TH_{value}(x)$ that yields 1 when the number that is represented in the vector of binary variables x is larger than or equal to value. For example, $TH_{value}(X)$ may be the following:

$TH_5(0, 0, 0)=0$
$TH_5(0, 0, 1)=0$
$TH_5(0, 1, 0)=0$
$TH_5(0, 1, 1)=0$
$TH_5(1, 0, 0)=0$
$TH_5(1, 0, 1)=1$
$TH_5(1, 1, 0)=1$
$TH_5(1, 1, 1)=1$

According to the method, a BDD of a Boolean function $TH_{value}(x)$ may be generated by:

```
BDD threshold(value, bits)
{
    result = 1
    while(bits>0)
    {
        bits = bits − 1
        if(value mod 2 = 1)
            result = result AND var_bits
        else
            if(result <> 1)
                result = result OR var_bits
        value = value / 2
    }
    return result
}
```

The generated BDD may be used to count the number of instances where the number that is represented in the vector of binary variables x is larger than or equal to value. As another example, if samples where sensor j has values between A and B are requested, the following query function may be used: $f_R(\vec{t}; \vec{s}^1; \ldots; \vec{s}^N) = TH_{\{A\}}(\vec{s}^j) \text{ AND } \overline{TH}_{\{B+1\}}(\vec{s}^j)$. As another example, if the requested values are all sensor values, the query function may be blank.

The query function and the characteristic function are used at step 218 to yield search results. The query function and the characteristic function may be used in any suitable manner. In certain embodiments, the query function and the characteristic function may be logically combined by applying a logical operation (such as a logical AND operation) to the functions. For example, characteristic function $f^S$ may be ANDed with query function $f_R(\vec{t}) = \bar{x}_1\bar{x}_2\bar{3}_3\ldots\bar{x}_{24}$. Applying a logical AND operation to a number of operands may yield the logical AND of the operands. The search results may be one or more samples that have the requested values or may be the number of samples that have the requested values.

In certain embodiments, the number of samples that have the requested values may be determined. The number may be determined in any suitable manner. For example, Boolean function $TH_{value}(x)$ may yield 1 when the number that is represented in the vector of binary variables x is larger than or equal to value. The number of instances where a BDD representing $TH_{value}(x)$ yields 1 may be counted to determine the number of instances where x is larger than or equal to value.

The search results are reported at step 222. The search results may reported in any suitable manner. For example, the search results may be expressed as binary decision diagrams.

Figure 4:
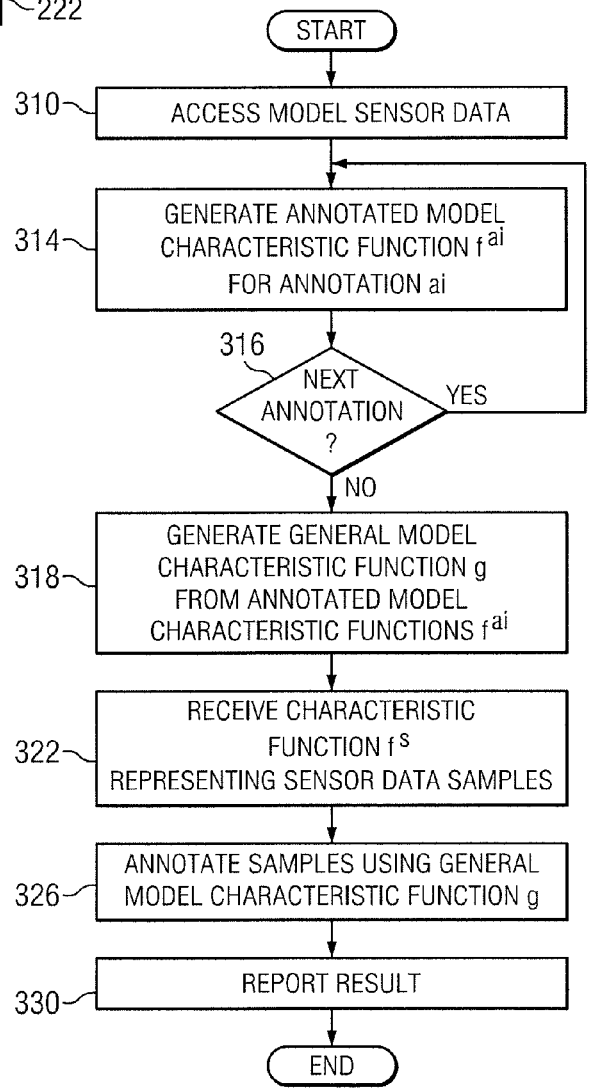
FIG. 4 illustrates an example of a method for annotating characteristic functions.

FIG. 4 illustrates an example of a method for annotating characteristic functions. The method may be performed by model engine 34. In the method, model sensor data is accessed at step 310. In certain embodiments, one or more sets of model samples of model sensor data 40 may be accessed. Each set comprises model samples for a corresponding annotation of one or more annotations.

Annotated model characteristic function $f^{ai}$ is generated for an annotation $a_i$ at step 314. Annotated model characteristic function $f^{ai}$ represents model samples annotated with one or more annotations. Annotated model characteristic function $f^{ai}$ may be used to identify measured samples that belong to the category indicated by the annotation.

Annotated model characteristic function $f^{ai}$ may be generated in any suitable manner. In certain embodiments, each model sample of annotation $a_i$ may be represented as a model minterm, and model characteristic function $f^{ai}$ may be generated from the model minterms by, for example, applying a logical operation (such as a logical OR operation) to the minterms. Model characteristic function $f^{ai}$ indicates whether a given minterm is a member of the model minterms.

In the embodiments, model characteristic function $f^{ai}$ may be annotated to yield annotated model characteristic function $f^{ai}$. Model characteristic function $f^{ai}$ may be annotated in any suitable manner. In certain embodiments, a Boolean variable is used to represent annotation $a_i$. A mathematical operation (such as the product operation) may be applied to the Boolean variable and the model characteristic function yield the annotated model characteristic function.

In an example scenario, time has a 32-bit resolution, and sensors have an 8-bit resolution. The $k^{th}$ sensor values [64, 127] at time [0,31] may be annotated with the normal attribute as follows:

$$f^{anormal}(\vec{t}; \vec{s}^1; \ldots; \vec{s}^k) = \bar{t}_{31}\bar{t}_{30}\ldots\bar{t}_6\bar{t}_5\bar{s}_7^k s_6^k$$

There may be a next annotation $a_{i+1}$ at step 316. If there is a next annotation $a_{i+1}$, the method returns to step 314 to generate a model characteristic function $f^{ai+1}$ for next annotation $a_{i+s}$. If there is no next annotation $a_{i+1}$, the method proceeds to step 318.

General model characteristic function g is generated from annotated model characteristic functions $f^a$ at step 318. General model characteristic function g may represent some or all sensor data 40. General model characteristic function g may be used to annotate samples of a given characteristic function, which is described in more detail below.

General model characteristic function g may be generated in any suitable manner. In certain embodiments, a logical operation (such as a logical OR operation) may be applied to annotated model characteristic functions $f^a$ to yield general model characteristic function g:

$$g(\vec{a};\vec{t};s^T;\ldots;s^{\vec{k}})=V_i f^{ai}$$

Characteristic function $f^S$ representing samples of sensor data 40 is received at step 322. The samples are annotated using the general model characteristic function g at step 326. The samples may be annotated in any suitable manner. In certain embodiments, a mathematical operation (such as a product operation) may be applied to the characteristic function and the general model characteristic function to annotate the samples:

$$f^{Q=fS} \cdot g$$

Annotated characteristic function $f^Q$ represents samples of characteristic function g annotated with annotations.

Core operations may be performed on annotated characteristic function $f^Q$. In certain embodiments, annotated characteristic function $f^Q$ may be queried to identify samples that have a particular annotation. For example, a density query can provide information on the percentage of data points annotated as with a particular annotation. As another example, the time range of data points with a particular annotation can be computed.

The query may be performed in any suitable manner, such as a manner substantially similar to that described herein. For example, a query function representing a given annotation may be formulated. The query function and the annotated characteristic function may then be combined to identify the samples.

The results are reported at step 330. The results may be reported in any suitable manner. For example, the results may be reported through interface 20.

Figure 5:
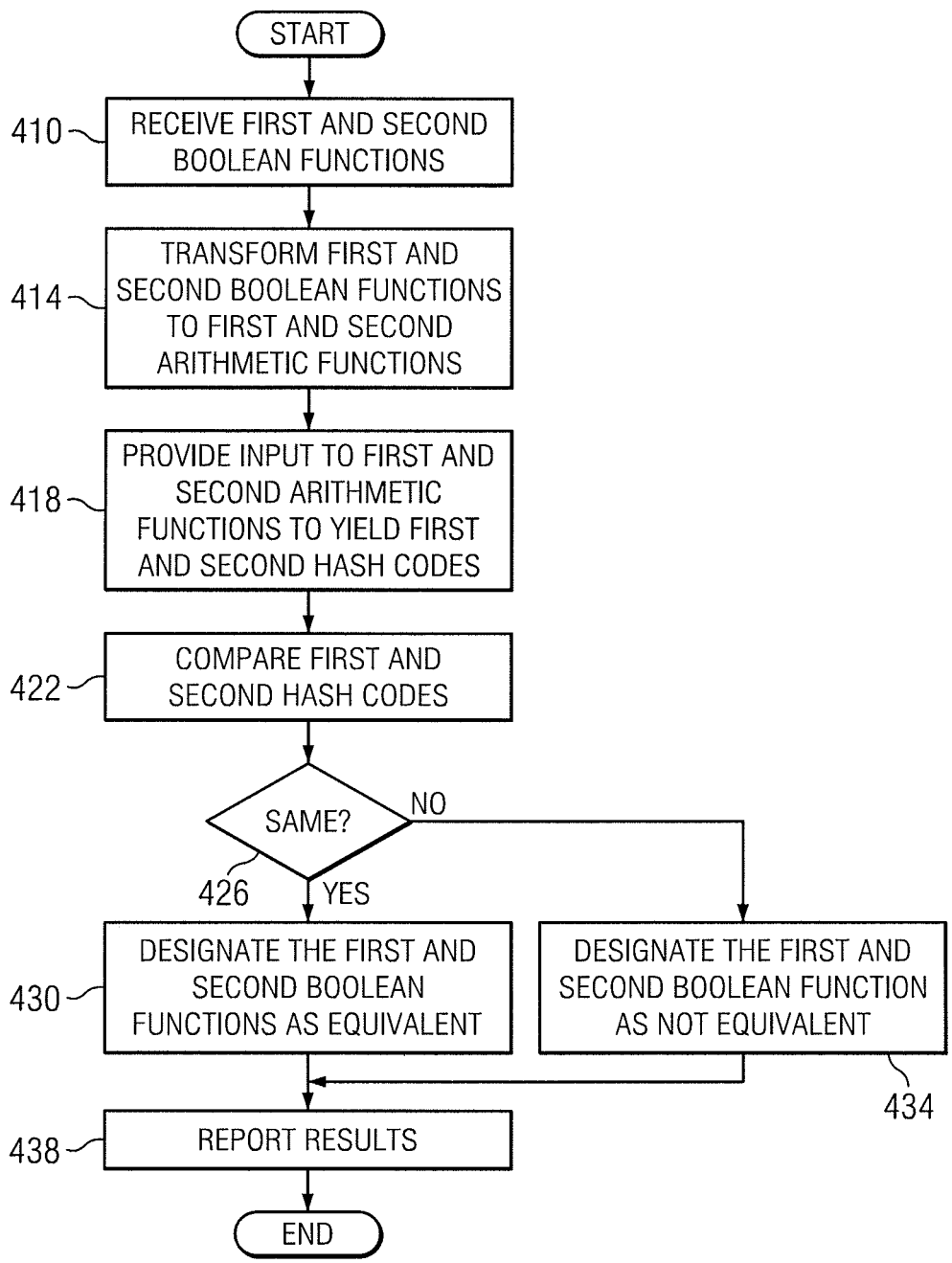
FIG. 5 illustrates an example of a method for determining whether characteristic functions are equivalent.

FIG. 5 illustrates an example of a method for determining whether Boolean functions (such as characteristic functions) are equivalent. The method may be performed by signature engine 36.

Signature engine 36 receives a first Boolean function and a second Boolean function at step 410.

The first Boolean function and the second Boolean function are transformed to a first arithmetic function and a second arithmetic function, respectively, at step 414. The Boolean functions may be transformed in any suitable manner. For example, the transformations may be performed according to one or more of the following rules:

X AND Y→X×Y
X OR Y→X+Y−X×Y
NOT(X)→1−X
X AND X (idempotence)→X×X=X; $X^k=X$ where → represents "is transformed to", AND represents logical AND, OR represents logical OR, NOT represents logical negation, X AND X represents idempotence, × represents multiplication, + represents addition, and a superscript represents an exponent. For example, if Boolean function F=X OR Y, then the arithmetic function A[F]=X+Y−X×Y. In certain examples, if the finite integer field has a size p, the arithmetic is performed modulo p.

In certain cases, a hash code H may be determined for a logical combination of Boolean functions B1 and B2. Hash code H may be determined from an arithmetic combination of hash codes H1 and H2, where H1 is the hash code of Boolean function B1 and H2 is the hash code of Boolean function B2. For example, the theorem of orthogonality may be applied. If Boolean functions B1 and B2 do not overlap in time, then hash code H for B1 V B2=H1+H2=H.

The same input is provided to the first arithmetic function and the second arithmetic function to calculate a first hash code and a second hash code, respectively, at step 418. Any suitable input may be used. In certain embodiments, the input may be randomly generated integers. In the example, if input X=5, Y=7 is provided to arithmetic function A[F]=X+Y−X×Y, then hash code is A[F]=5+7−5×7=−23.

The first and second hash codes are compared at step 422. The first and second hash codes may be equal or not equal at step 426. Hash codes of equivalent functions are the same, and hash codes of different functions are probably different. If arithmetic expressions are evaluated in a finite integer field under randomization, then any distinct pair of $2^{2^n}$ Boolean functions almost always maps to distinct hash codes. The probability of error is n/(size-of-integer-field), where integer field $Z_p=\{0, 1, \ldots, p-1\}$ and p is prime. As prime p increases, the probability of error decreases and may be practically close to 0. Accordingly, a larger prime p may be selected to yield more accurate hash codes, and a smaller prime p may be selected to yield less accurate hash codes. In certain embodiments, hash codes may be repeatedly generated to improve accuracy. Error decreases exponentially after each run. After k runs, error e≤$(n/p)^k$.

If the first hash code equals the second hash code at step 426, the method proceeds to step 430, where signature engine 36 designates the first Boolean function and the second Boolean function as equivalent. If the first hash code does not equal the second hash code, the method proceeds to step 434, where signature engine 36 designates the first Boolean function and the second Boolean function as not equivalent.

Results are reported at step 438. The results may be reported using interface 20.

Examples of the method may be used in any suitable application. As an example, hash codes may be used to verify communication of Boolean functions or BDDs over a communication link (wired and/or wireless) to a network node (such as a base station). A sending node may send Boolean functions and hash codes of the Boolean functions to a receiving node after every K blocks of data of the Boolean functions. The hash codes may be encrypted. Multiple hash codes may be sent or the same hash code may be sent multiple times.

The receiving node may calculate a hash code for a Boolean function and compare the calculated hash code with the hash code received with the Boolean function. If the hash codes are the same, the receiving node may determine that the Boolean function is valid, for example, has been properly received. Otherwise, the receiving node may determine that the Boolean function is not valid, for example, has not been properly received and may have been corrupted.

As another example, hash codes may be used to mark and later validate data stored as Boolean functions or BDDs. A hash code may be calculated for a Boolean function and may be stored with or separately from the Boolean function. At a later time, the Boolean function may be validated using the stored hash function. A new hash code may be calculated for the Boolean function and compared with the stored hash code. If the hash codes are the same, the Boolean function may be regarded as valid, such as uncorrupted. Otherwise, the Boolean function may be regarded as invalid, such as corrupted.

More accurate hash codes may be used to mark more important data, and less accurate hash codes may be used to mark less important data. Less accurate hash codes may be used if processing power is limited, such as for storage in mobile phones.

Modifications, additions, or omissions may be made to the systems and apparatuses disclosed herein without departing from the scope of the invention. The components of the systems and apparatuses may be integrated or separated. Moreover, the operations of the systems and apparatuses may be performed by more, fewer, or other components. For example, the operations of BDD generator 30 and query engine 32 may be performed by one component, or the operations of BDD generator 30 may be performed by more than one component. Additionally, operations of the systems and apparatuses may be performed using any suitable logic comprising software, hardware, and/or other logic. As used in this document, "each" refers to each member of a set or each member of a subset of a set.

Modifications, additions, or omissions may be made to the methods disclosed herein without departing from the scope of the invention. The methods may include more, fewer, or other steps. Additionally, steps may be performed in any suitable order.

A component of the systems and apparatuses disclosed herein may include an interface, logic, memory, and/or other suitable element. An interface receives input, sends output, processes the input and/or output, and/or performs other suitable operation. An interface may comprise hardware and/or software.

Logic performs the operations of the component, for example, executes instructions to generate output from input. Logic may include hardware, software, and/or other logic. Logic may be encoded in one or more tangible media and may perform operations when executed by a computer. Certain logic, such as a processor, may manage the operation of a component. Examples of a processor include one or more computers, one or more microprocessors, one or more applications, and/or other logic.

In particular embodiments, the operations of the embodiments may be performed by one or more computer readable media encoded with a computer program, software, computer executable instructions, and/or instructions capable of being executed by a computer. In particular embodiments, the operations of the embodiments may be performed by one or more computer readable media storing, embodied with, and/or encoded with a computer program and/or having a stored and/or an encoded computer program.

A memory stores information. A memory may comprise one or more non-transitory, tangible, computer-readable, and/or computer-executable storage media. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable medium.

Components of the systems and apparatuses may be coupled by any suitable communication network. A communication network may comprise all or a portion of one or more of the following: a public switched telephone network (PSTN), a public or private data network, a local area network (LAN), a metropolitan area network (MAN), a wide area network (WAN), a local, regional, or global communication or computer network such as the Internet, a wireline or wireless network, an enterprise intranet, other suitable communication link, or any combination of any of the preceding.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

What is claimed is:

1. A method for annotating large volumes of medical data represented by binary decision diagrams comprising, by one or more processors associated with one or more computer systems:

accessing a plurality of set of samples of sensor data recording a plurality of medical measurements taken by one or more medical sensors, wherein each set of the one or more sets of samples corresponds to an annotation used to categorize the sensor data;

representing each data value of the set of samples as a minterm to yield a set of minterms, each minterm within the set of minterms comprising a logical expression of one or more variables allocated to the data value of the sample;

generating a characteristic function from the set of minterms, the characteristic function being represented by a reduced ordered binary decision diagram indicating whether a given minterm is a member of the set of minterms, the reduced ordered binary decision diagram being stored compactly in a BDD library;

receiving a search query for a search of a set of samples of sensor data wherein the query indicates one or more requested values of one or more sensor parameters, the search query being represented by a query function corresponding to the requested values;

identifying one or more minterms of the set of minterms that are associated with a given medical annotation by combining the query function and the characteristic function through logical operations, the identified minterms counting the number of instances where the data value represented by the minterm of the set of minterms is equal to the one or more requested values; and reporting the results of said identifying as search results, through an interface.

2. The method of claim 1, the identifying the one or more minterms further comprising:

receiving a model characteristic function, the model characteristic function representing a set of model minterms annotated with one or more medical annotations; and identifying the one or more minterms using the model characteristic function and the characteristic function.

3. The method of claim 1, the identifying the one or more minterms further comprising:

annotating the characteristic function using a model characteristic function to yield an annotated characteristic function, the model characteristic function representing a set of model minterms annotated with one or more medical annotations; and querying the annotated characteristic function to identify the one or more minterms.

4. The method of claim 1, the identifying the one or more minterms further comprising:
    annotating the characteristic function using a model characteristic function to yield an annotated characteristic function, the model characteristic function representing a set of model minterms annotated with one or more medical annotations, the annotated characteristic function representing the set of minterms annotated with the one or more medical annotations; and
    querying the annotated characteristic function to identify the one or more minterms.

5. The method of claim 1, the identifying the one or more minterms further comprising:
    determining an annotated characteristic function for the characteristic function, the annotated characteristic function representing the set of minterms annotated with one or more medical annotations;
    formulating a query BDD representing the given medical annotation; and
    applying a logical AND operation to the query BDD and the annotated characteristic function to identify the one or more minterms.

6. The method of claim 1, the one or more medical annotations comprising one or more of the following: a normal annotation or an abnormal annotation.

7. The method of claim 1, wherein the samples of sensor data comprise a set of numerical values recording the plurality of medical measurements, and wherein the method further comprises:
    allocating a variable to each numerical value within the set of numerical values to create a minterm for each numerical value;
    for each numerical value within the set of numerical values, converting each minterm to a binary number, and
    applying a logic operation to a plurality of binary numbers representing the set of samples to generate the characteristic function.

8. The method of claim 1, further comprising:
    accessing a next set of samples of sensor data recording an additional plurality of medical measurements; and
    updating the characteristic function based on the next set of samples.

9. The method of claim 1, wherein the reduced ordered binary decision diagram comprises one or more rooted directed acyclic graphs representing a Boolean function.

10. The method of claim 1, wherein the reduced ordered binary decision diagram comprises a plurality of nodes and a plurality of edges connecting the nodes thereby forming a plurality of paths, each path in the binary decision diagram representing a set of variable assignments setting a Boolean function represented by the binary decision diagram to either 1 or 0.

11. An apparatus for annotating large volumes of medical data represented by binary decision diagrams comprising: one or more processors; and a memory coupled to the processors comprising instructions executable by the processors, the processors operable when executing the instructions to:
    access a plurality of set of samples of sensor data recording a plurality of medical measurements taken by one or more medical sensors, wherein each set of the one or more sets of samples corresponds to an annotation used to categorize the sensor data;
    represent each data value of the set of samples as a minterm to yield a set of minterms, each minterm within the set of minterms comprising a logical expression of one or more variables allocated to the data value of the sample;
    generate a characteristic function from the set of minterms, the characteristic function being represented by a reduced ordered binary decision diagram indicating whether a given minterm is a member of the set of minterms, the reduced ordered binary decision diagram being stored compactly in a BDD library;
    receive a search query for a search of a set of samples of sensor data wherein the query indicates one or more requested values of one or more sensor parameters, the search query being represented by a query function corresponding to the requested values;
    identify one or more minterms of the set of minterms that are associated with a given medical annotation by combining the query function and the characteristic function through logical operations, the identified minterms counting the number of instances where the data value represented by the minterm of the set of minterms is equal to the one or more requested values; and
    report the results of said identifying as search results, through an interface.

12. The apparatus of claim 11, the identifying the one or more minterms further comprising:
    receiving a model characteristic function, the model characteristic function representing a set of model minterms annotated with one or more medical annotations; and
    identifying the one or more minterms using the model characteristic function and the characteristic function.

13. The apparatus of claim 11, the identifying the one or more minterms further comprising:
    annotating the characteristic function using a model characteristic function to yield an annotated characteristic function, the model characteristic function representing a set of model minterms annotated with one or more medical annotations; and
    querying the annotated characteristic function to identify the one or more minterms.

14. The apparatus of claim 11, the identifying the one or more minterms further comprising:
    annotating the characteristic function using a model characteristic function to yield an annotated characteristic function, the model characteristic function representing a set of model minterms annotated with one or more medical annotations, the annotated characteristic function representing the set of minterms annotated with the one or more medical annotations; and
    querying the annotated characteristic function to identify the one or more minterms.

15. The apparatus of claim 11, the identifying the one or more minterms further comprising:
    determining an annotated characteristic function for the characteristic function, the annotated characteristic function representing the set of minterms annotated with one or more medical annotations;
    formulating a query BDD representing the given medical annotation; and
    applying a logical AND operation to the query BDD and the annotated characteristic function to identify the one or more minterms.

16. The apparatus of claim 11, the one or more medical annotations comprising one or more of the following: a normal annotation or an abnormal annotation.

17. One or more non-transitory computer-readable media storing code for annotating large volumes of medical data represented by binary decision diagrams, when executed by one or more processors, configured to:
    access a plurality of set of samples of sensor data recording a plurality of medical measurements taken by one or more medical sensors, wherein each set of the one or more sets of samples corresponds to an annotation used to categorize the sensor data;

represent each data value of the set of samples as a minterm to yield a set of minterms, each minterm within the set of minterms comprising a logical expression of one or more variables allocated to the data value of the sample;

generate a characteristic function from the set of minterms, the characteristic function being represented by a reduced ordered binary decision diagram indicating whether a given minterm is a member of the set of minterms, the reduced ordered binary decision diagram being stored compactly in a BDD library;

receive a search query for a search of a set of samples of sensor data wherein the query indicates one or more requested values of one or more sensor parameters, the search query being represented by a query function corresponding to the requested values;

identify one or more minterms of the set of minterms that are associated with a given medical annotation by combining the query function and the characteristic function through logical operations, the identified minterms counting the number of instances where the data value represented by the minterm of the set of minterms is equal to the one or more requested values; and report the results of said identifying as search results, through an interface.

18. The media of claim 17, the identifying the one or more minterms further comprising:
receiving a model characteristic function, the model characteristic function representing a set of model minterms annotated with one or more medical annotations; and
identifying the one or more minterms using the model characteristic function and the characteristic function.

19. The media of claim 17, the identifying the one or more minterms further comprising:
annotating the characteristic function using a model characteristic function to yield an annotated characteristic function, the model characteristic function representing a set of model minterms annotated with one or more medical annotations; and
querying the annotated characteristic function to identify the one or more minterms.

20. The media of claim 17, the identifying the one or more minterms further comprising:
annotating the characteristic function using a model characteristic function to yield an annotated characteristic function, the model characteristic function representing a set of model minterms annotated with one or more medical annotations, the annotated BDD representing the set of minterms annotated with the one or more medical annotations; and
querying the annotated characteristic function to identify the one or more minterms.

21. The media of claim 17, the identifying the one or more minterms further comprising:
determining an annotated characteristic function for the characteristic function, the annotated characteristic function representing the set of minterms annotated with one or more medical annotations;
formulating a query BDD representing the given medical annotation; and
applying a logical AND operation to the query BDD and the annotated characteristic function to identify the one or more minterms.

22. The media of claim 17, the one or more medical annotations comprising one or more of the following: a normal annotation or an abnormal annotation.

* * * * *